United States Patent
Sun et al.

(10) Patent No.: US 11,732,202 B1
(45) Date of Patent: *Aug. 22, 2023

(54) INTEGRATION PROCESS FOR PYROLYSIS OIL UPGRADING WITH MAXIMIZED BTX YIELD

(71) Applicant: Saudi Arabia Oil Company, Dhahran (SA)

(72) Inventors: Miao Sun, Dhahran (SA); Zhonglin Zhang, Dhahran (SA); Noor Al-Mana, Dhahran (SA); Hattan T. Janbi, Dhahran (SA); Sohel K. Shaikh, Dhahran (SA); Eman Z. Albaher, Dhahran (SA); Noor A. Sulais, Dammam (SA)

(73) Assignee: Saudi Arabia Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/703,381

(22) Filed: Mar. 24, 2022

(51) Int. Cl.
*C10G 69/00* (2006.01)
*C10G 69/12* (2006.01)
(Continued)

(52) U.S. Cl.
CPC .......... *C10G 69/123* (2013.01); *B01J 29/045* (2013.01); *C10G 9/36* (2013.01); *C10G 35/095* (2013.01);
(Continued)

(58) Field of Classification Search
CPC ...... C10G 69/123; C10G 9/36; C10G 35/095; C10G 45/50; C10G 45/54; C10G 45/56;
(Continued)

(56) References Cited

U.S. PATENT DOCUMENTS 3,843,740 A   10/1974 Mitchell et al.
3,953,366 A   4/1976 Morrison
(Continued)

FOREIGN PATENT DOCUMENTS

JP   S6341592 A   2/1988

OTHER PUBLICATIONS

Guerzoni et al., "Catalytic Cracking of a Hydrocarbon Mixture on Combinations of HY and HZSM-5 Zeolites", Journal of Catalysis, vol. 139, pp. 289-303, 1993.
(Continued)

*Primary Examiner* — Prem C Singh
*Assistant Examiner* — Brandi M Doyle
(74) *Attorney, Agent, or Firm* — Dinsmore & Shohl LLP (57) ABSTRACT

A method for producing aromatic compounds from pyrolysis oil comprises: upgrading the pyrolysis oil to pyrolysis gasoline in a multi-stage reactor comprising a slurry-phase reactor and a fixed-bed reactor, wherein the slurry-phase reactor comprises a mixed metal oxide catalyst, and the fixed-bed reactor comprises a mesoporous zeolite-supported metal catalyst; aromatizing the pyrolysis gasoline in an aromatization unit; hydrodealkylating and transalkylating a product from the aromatization unit in a hydrodealkylation-transalkylation unit, thereby producing an aromatic stream; and processing the aromatic stream in an aromatics recovery complex to produce the aromatic compounds comprising benzene, toluene, and xylenes (BTX).

15 Claims, 4 Drawing Sheets

(51) Int. Cl.

| | |
|---|---|
| *C10G 45/56* | (2006.01) |
| *C10G 45/54* | (2006.01) |
| *C10G 45/50* | (2006.01) |
| *C10G 45/64* | (2006.01) |
| *C10G 35/095* | (2006.01) |
| *C10G 9/36* | (2006.01) |
| *B01J 29/04* | (2006.01) |
| *C10G 65/08* | (2006.01) |

(52) U.S. Cl.
CPC ............ *C10G 45/50* (2013.01); *C10G 45/54* (2013.01); *C10G 45/56* (2013.01); *C10G 45/64* (2013.01); *C10G 65/08* (2013.01); *C10G 2300/1096* (2013.01); *C10G 2300/4006* (2013.01); *C10G 2300/4012* (2013.01); *C10G 2300/4018* (2013.01); *C10G 2300/4081* (2013.01); *C10G 2300/70* (2013.01); *C10G 2400/30* (2013.01)

(58) Field of Classification Search
CPC .............. C10G 45/64; C10G 65/08; C10G 2300/1096; C10G 2300/4006; C10G 2300/4012; C10G 2300/4018; C10G 2300/4081; C10G 2300/70; C10G 2400/30; B01J 29/045
See application file for complete search history.

(56) References Cited

U.S. PATENT DOCUMENTS

| | | |
|---|---|---|
| 4,304,657 A | 12/1981 | Miller |
| 4,499,316 A | 2/1985 | Garska et al. |
| 5,895,828 A | 4/1999 | Yao et al. |
| 5,898,089 A | 4/1999 | Drake et al. |
| 6,635,792 B2 | 10/2003 | Choi et al. |
| 9,181,146 B2 | 11/2015 | Iaccino et al. |
| 9,181,147 B2 | 11/2015 | Iaccino et al. |
| 10,751,709 B1 | 8/2020 | Sun et al. |
| 10,751,710 B1 | 8/2020 | Sun |
| 10,793,794 B2 | 10/2020 | Al-Ghamdi et al. |
| 10,835,894 B1 | 11/2020 | Sun et al. |
| 11,377,400 B1* | 7/2022 | Sun .................... B01J 29/48 |
| 2016/0362616 A1* | 12/2016 | Oprins .................. C10G 49/22 |
| 2020/0017773 A1 | 1/2020 | Ramamurthy et al. |
| 2021/0001320 A1 | 1/2021 | Sun |
| 2021/0130716 A1 | 5/2021 | Xu et al. |

OTHER PUBLICATIONS

Jimenez-Cruz et al., "Molecular size evaluation of linear and branched paraffins from the gasoline pool by DFT quantum chemical calculations", Fuel, vol. 83, pp. 2813-2188, 2004.

Kim et al., "Novel Ni2P/zeolite catalysts for naphthalene hydrocracking to BTX", Catalysis Communications, vol. 45, pp. 133-138, 2014.

Kim et al., "Morphology effect of B-Zeolite supports for Ni2P catalysts on the hydrocracking of polycyclic aromatic hydrocarbons to benzene, toluene, and xylene", Journal of Catalysis, vol. 351, pp. 67-78, 2017.

Kondoh et al., "Effects of H2O Addition on Oil Sand Bitumen Cracking Using a CeO2—ZrO2—Al2O3—FeOx Catalyst", Energy & Fuels, vol. 30, p. 10358-10364, 2016.

Kondoh et al., "Upgrading of oil sand bitumen over an iron oxide catalyst using sub- and super-critical water", Fuel Processing Technology, vol. 145, pp. 96-101, 2016.

Kondoh et al., "Catalytic cracking of heavy oil over TiO2—ZrO2 catalysts under superheated steam conditions", Fuel, vol. 167, pp. 288-294, 2016.

Lapinas et al., "Catalytic Hydrogenation and Hydrocracking of Fluorene: Reaction Pathways, Kinetics, and Mechanisms", Ind. Eng. Chem. Res., vol. 30, No. 1, pp. 42-50, 1991.

Leite et al., "Hydrocracking of phenanthrene over bifunctional Pt catalysts", Catalysis Today, vol. 65, pp. 241-247, 2001.

Lemberton et al., "Catalytic hydroconversion of simulated coal tars", Applied Catalysis A: General, vol. 79, pp. 115-126, 1991.

Matsui, "Explanation of Product Distribution of Hydrocracking Reaction of Aromatic Hydrocarbons with Nickel-Loaded Zeolites Based on CAMD Study on Interaction between Zeolites and Substrates", Energy & Fuels, vol. 9, pp. 435-438, 1995.

Park et al., "Hydro-conversion of 1-methyl naphthalene into (alkyl)benzenes over alumina-coated USY zeolite-supported NiMoS catlysts", Fuel, vol. 90, pp. 182-189, 2011.

Park et al., "Mild hydrocracking of 1-methyl naphthalene (1-MN) over alumina modified zeolite", Journal of Industrial and Engineering Chemistry, vol. 19, pp. 627-632, 2013.

Tailleur et al., "The effect of aromatics on paraffin mild hydrocracking reactions (WNiPd/CeY—Al2O3)", Fuel Processing Technology, vol. 89, pp. 808-818, 2008.

Notification of Transmittal of the International Search Report and Written Opinion of the International Searching Authority, or the Declaration dated Dec. 5, 2022 pertaining to International application No. PCT/US2022/043435 filed Sep. 14, 2022, 11 pages.

* cited by examiner

INTEGRATION PROCESS FOR PYROLYSIS OIL UPGRADING WITH MAXIMIZED BTX YIELD

FIELD

Embodiments of the present disclosure generally relate to refining and upgrading hydrocarbon oil, and pertain particularly to a process producing aromatic compounds from pyrolysis gasoline.

TECHNICAL BACKGROUND

To maximize refinery-petrochemicals integration benefits and to meet the stringent fuel specification, the valorization of intermediate petrochemicals/refinery streams to petrochemical building blocks has gained more attention in the last few years. Meanwhile, the market demand for aromatics, which serve as basic building blocks and intermediates in the petrochemical industry, has been growing steadily and the market price for these petrochemicals has shown tangible dependence on naphtha and crude prices in the past decades. This trend has pushed researchers to look for alternative cheaper feedstock for aromatics manufacturing, creating an opportunity and a potential market for technologies that produce aromatic building blocks from cheap industrial intermediate streams.

In a typical steam pyrolysis process, a heavy byproduct stream comes out as a bottom layer from the steam cracker, which is referred to as pyrolysis oil. This heavy stream has low sulfur but very rich in aromatic contents; however, it has limited applications and it is normally burned as fuel oil. With a high number of aromatics, this cheap pyrolysis oil can make an ideal feedstock for the production of valuable intermediate petrochemicals, such as benzene, toluene and xylenes (BTX).

SUMMARY

Therefore, there is a continual need for systems and processes for recovering an increased amount of aromatics. The present embodiments are directed to upgrading pyrolysis oil in a continuous system to maximize BTX yield. The system enables the increase of pyrolysis gasoline production at the expense of pyrolysis oil to maximize the production of BTX.

According to an embodiment, a method for producing aromatic compounds from pyrolysis oil comprises: upgrading the pyrolysis oil to pyrolysis gasoline in a multi-stage reactor comprising a slurry-phase reactor and a fixed-bed reactor, wherein the slurry-phase reactor comprises a mixed metal oxide catalyst, and the fixed-bed reactor comprises a mesoporous zeolite-supported metal catalyst; aromatizing the pyrolysis gasoline in an aromatization unit; hydrodealkylating and transalkylating a product from the aromatization unit in a hydrodealkylation-transalkylation unit, thereby producing an aromatic stream; and processing the aromatic stream in an aromatics recovery complex to produce the aromatic compounds comprising benzene, toluene, and xylenes (BTX).

Additional features and advantages of the embodiments described herein will be set forth in the detailed description, which follows, and in part will be readily apparent to those skilled in the art from that description or recognized by practicing the embodiments described, including the detailed description and the claims, which are provided infra.

BRIEF DESCRIPTION OF THE DRAWINGS

The following detailed description of specific embodiments of the present disclosure can be best understood when read in conjunction with the following drawings in which.

Figure (FIG. 1 is a schematic illustration of the systems and processes of the present disclosure.

DETAILED DESCRIPTION

As used herein, the term "hydrocarbon oil" or "hydrocarbon feedstock" refers to an oily liquid composed mostly of a mixture of hydrocarbon compounds. Hydrocarbon oil may include refined oil obtained from crude oil, synthetic crude oil, bitumen, oil sand, shale oil, or coal oil. The term "refined oil" includes, but is not limited to, vacuum gas oil (VGO), deasphalted oil (DAO) obtained from a solvent deasphalting process, demetallized oil (DMO), light and/or heavy coker gas oil obtained from a coker process, cycle oil obtained from a fluid catalytic cracking (FCC) process, and gas oil obtained from a visbreaking process.

As used herein, the term "hydrocarbon" refers to a chemical compound composed entirely of carbon and hydrogen atoms. An expression such as "$C_x$-$C_y$ hydrocarbon" refers to a hydrocarbon having from x to y carbon atoms. For instance, a $C_1$-$C_5$ hydrocarbon includes methane, ethane, propane, the butanes, and the pentanes.

As used herein, the term "liquid hourly space velocity" or "LHSV" refers to the ratio of the liquid flow rate of the hydrocarbon feed to the catalyst volume or mass.

As used herein, the term "weight hourly space velocity" or "WHSV" refers to the ratio of the weight of reagent flow to the catalyst weight.

As used herein, the term "conduit" includes casings, liners, pipes, tubes, coiled tubing, and mechanical structures with interior voids.

As used herein, the term "hydrogen/oil ratio" or "hydrogen-to-oil ratio" or "hydrogen-to-hydrocarbon ratio" refers to a standard measure of the volume rate of hydrogen circulating through the reactor with respect to the volume of feed. The hydrogen/oil ratio may be determined by comparing the flow volume of the hydrogen gas stream and the flow volume of the hydrocarbon feed.

As used herein, the term "decreased content" of a substance means that a concentration of the substance is greater before passing through a stage of the process under examination than it is after passing through the stage. As used herein, the term "increased content" of a substance means that a concentration of the substance is greater after passing through a stage of the process under examination than before passing through the stage.

As used herein, any stream that is referred to as "rich" in some chemical species contains 50% or more by volume of that chemical species.

As used throughout this disclosure, "zeolites" may refer to micropore-containing inorganic materials with regular intra-crystalline cavities and channels of molecular dimension. Zeolites generally comprise a crystalline structure, as opposed to an amorphous structure such as what may be observed in some porous materials such as amorphous silica. Zeolites generally include a microporous framework, which may be identified by a framework type. The microporous structure of zeolites (e.g., 0.3 nm to 2 nm pore size) may render large surface areas and desirable size-/shape-selectivity, which may be advantageous for catalysis. The zeolites described may include, for example, aluminosilicates, titanosilicates, or pure silicates. In embodiments, the zeolites described may include micropores (present in the microstructure of a zeolite), and additionally include mesopores. As used throughout this disclosure, micropores refer to pores in a structure that have a diameter of greater than or equal to 0.1 nm and less than or equal to 2 nm, and mesopores refer to pores in a structure that have a diameter of greater than 2 nm and less than or equal to 50 nm. Unless otherwise described herein, the "pore size" of a material refers to the average pore size, but materials may additionally include micropores and/or mesopores having a particular size that is not identical to the average pore size.

In accordance with one or more embodiments, a method for producing aromatic compounds from pyrolysis oil comprises: upgrading the pyrolysis oil to pyrolysis gasoline in a multi-stage reactor comprising a slurry-phase reactor and a fixed-bed reactor, wherein the slurry-phase reactor comprises a mixed metal oxide catalyst, and the fixed-bed reactor comprises a mesoporous zeolite-supported metal catalyst. The method further comprises: aromatizing the pyrolysis gasoline in an aromatization unit; hydrodealkylating and transalkylating a product from the aromatization unit in a hydrodealkylation-transalkylation unit, thereby producing an aromatic stream; and processing the aromatic stream in an aromatics recovery complex to produce the aromatic compounds comprising benzene, toluene, and xylenes (BTX).

Figure 1:
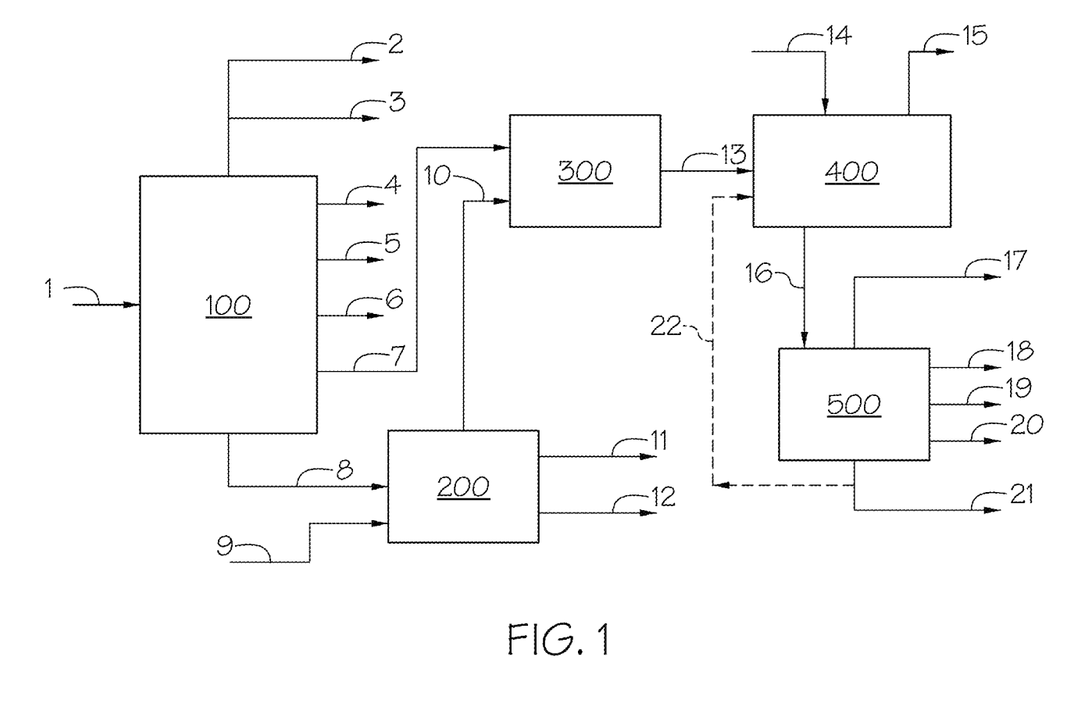

Referring to FIG. 1, a hydrocarbon feedstock 1 is delivered to a steam cracker and fractionation unit 100. The steam cracker and fractionation unit 100 produces multiple product streams including hydrogen 2, fuel gas 3, ethylene 4, propylene 5, butane 6, pyrolysis gasoline 7, and pyrolysis oil 8. The pyrolysis oil 8 is discharged from the bottoms of the steam cracker 100.

Figure 2:
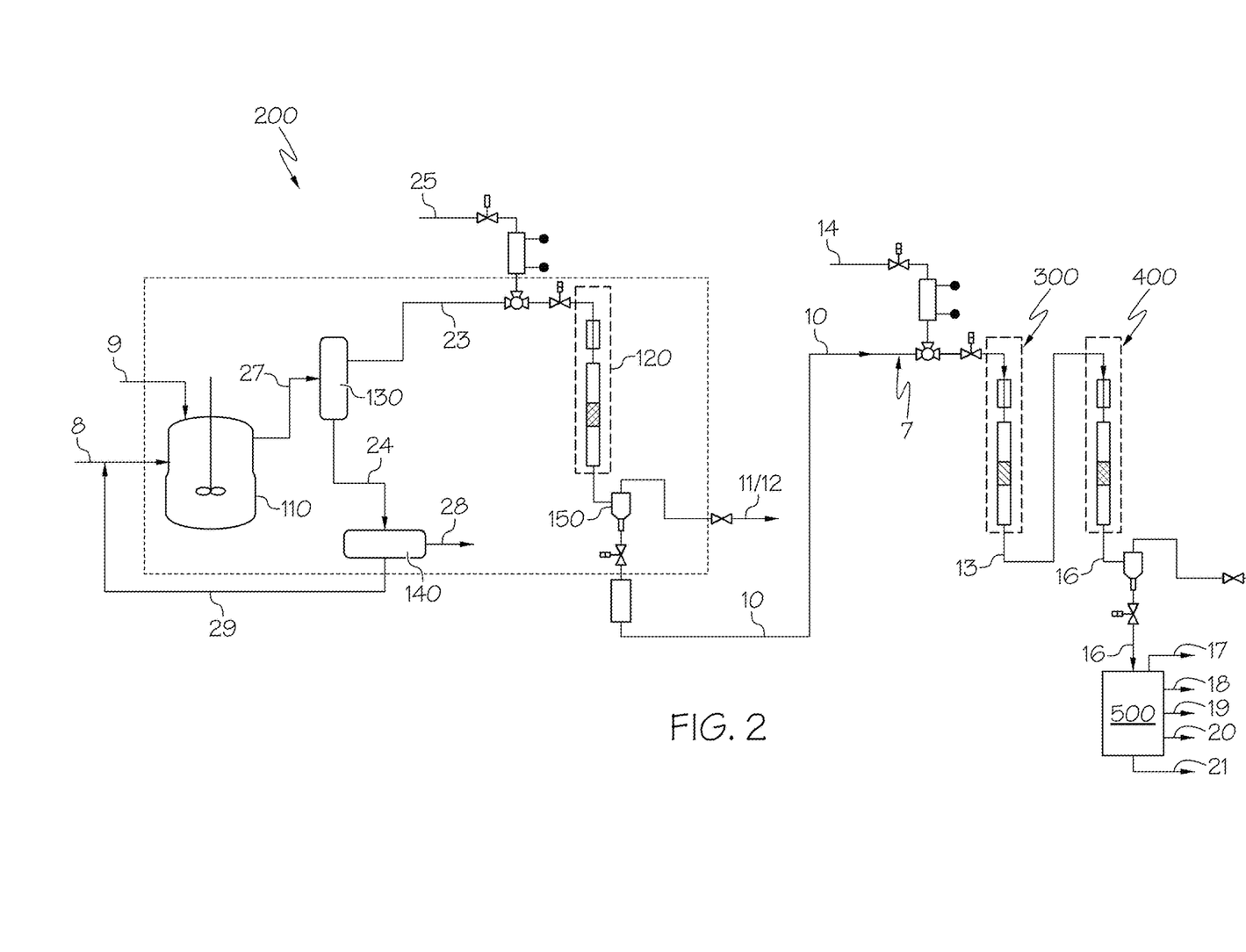
FIG. 2 is another schematic illustration of the systems and processes of the present disclosure.

The pyrolysis oil 8 is delivered to a multi-stage reactor 200, which produces pyrolysis gas 10. Referring to FIG. 2, the multi-stage reactor 200 comprises a slurry-phase reactor 110 and a fixed-bed reactor 120, which is downstream of the slurry-phase reactor 110. The slurry-phase reactor 110 may include a mixed metal oxide catalyst, and the fixed-bed reactor comprises a mesoporous zeolite-supported metal catalyst, which are both described in more detail below.

The pyrolysis oil 8, optionally with a diluent, is fed to the slurry-phase reactor 110. The pyrolysis oil 8, which comprises polyaromatics, are contacted with the mixed metal oxide catalysts while hydrogen gas 9 is added to the slurry-phase reactor 110. In embodiments, the mixed metal oxide catalysts may be added simultaneously with the pyrolysis oil 8 so that a liquid phase and a solid phase may be mixed to produce the slurry.

In embodiments, the pyrolysis oil, a diluent, hydrogen, and the mixed metal oxide catalyst are added to a slurry-phase reactor. The components may be added simultaneously in some embodiments, or at different times in other embodiments. The reactor may be agitated. In embodiments, the agitation may comprise stirring. In other embodiments, the agitation may comprise shaking. In embodiments, the reactor may be agitated via stirring and shaking.

Figure 3:
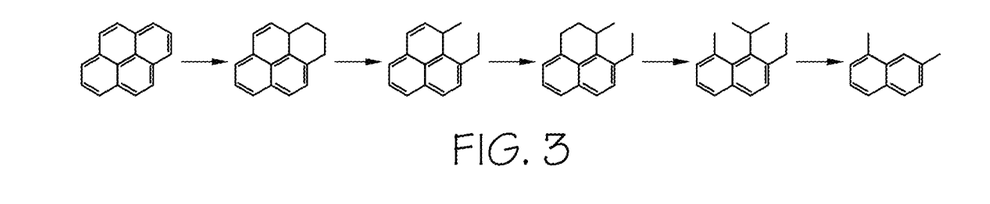
FIG. 3 is a diagram of chemical processes performed in the pyrolysis oil upgrading according to one or more embodiments of the present disclosure.

In operation, the pyrolysis oil 8 undergoes continuous selective hydrogenation, selective opening of saturated rings, hydro-dealkylation, trans-alkylation, and disproportionation produce di-aromatic intermediates in the slurry effluent 27 of the slurry-phase reactor 110. An example of a cascade of such reactions is shown in FIG. 3, beginning with pyrene and resulting in a methylated naphthalene. The formation of methylated naphthalene from pyrene is, of course, merely an example of the cascade of reactions, and other starting materials and products are contemplated.

Referring again to FIG. 2, after being allowed to react, the slurry effluent 27 may be transferred to separator 130 to remove used catalyst and heavy residue, thereby outputting a fixed-bed reactor feed 23, which comprises the di-aromatic intermediates, and a heavier stream 24 comprising used catalyst and heavy residues comprising residual polyaromatic compounds. The heavier stream 24 may be fed to a catalyst reclamation unit 140, wherein the used catalyst 28 is separated from the heavy residues 29. Optionally, the heavy residue 29 may be recycled back as a feed for the slurry-phase reactor 110.

The fixed-bed reactor feed 23 may include di-aromatic compounds and mono-aromatic compounds. Examples of di-aromatic compounds include, but are not limited to, naphthalene and tetralin, both of which may be unsubstituted or substituted with straight-chain or branched hydrocarbon substituents. Examples of mono-aromatic compounds include, but are not limited to, benzene, which may be unsubstituted or substituted with straight-chain or branched hydrocarbon substituents In embodiments, the pyrolysis oil may include one or more polyaromatic compounds. The polyaromatic compounds may include one or more aromatic carbon atoms ($C_{16}+$), such as $C_{16}$-$C_{110}$ polyaromatic compounds. For instance, the polyaromatic compounds may be $C_{16}$-$C_{100}$, $C_{16}$-$C_{90}$, $C_{16}$-$C_{80}$, $C_{16}$-$C_{70}$, $C_{16}$-$C_{60}$, $C_{16}$-$C_{50}$, $C_{16}$-$C_{40}$, $C_{16}$-$C_{30}$, $C_{16}$-$C_{20}$, $C_{20}$-$C_{110}$, $C_{30}$-$C_{110}$, $C_{40}$-$C_{110}$, $C_{50}$-$C_{110}$, $C_{60}$-$C_{110}$, $C_{70}$-$C_{110}$, $C_{80}$-$C_{110}$, $C_{90}$-$C_{110}$, or even $C_{100}$-$C_{110}$ polyaromatic compounds.

In embodiments, the polyaromatic compounds may include multiple fused aromatic rings, such as 3, 4, 5, 6, 7, 8, 9, or 10 fused benzene rings.

In embodiments, the diluent may be an organic solvent, such as toluene, benzene, or a combination of toluene and benzene. Without intending to be bound by any particular theory, it is believed that the diluent increases the fluidity of the pyrolysis oil feed such that raw pyrolysis oil may have better contact with the mixed metal oxide catalysts than would be possible without the diluent.

Conditions of the slurry-phase reactor 110, such as flow rate into the reactor, temperature in the reactor, and pressure in the reactor may be varied to control the reactions. In embodiments, the flow rate of the hydrogen gas may be from 15 ml/min to 35 ml/min, such as from 20 ml/min to 35 ml/min, from 25 ml/min to 35 ml/min, from 30 ml/min to 35 ml/min, from 15 ml/min to 30 ml/min, from 15 ml/min to 25 ml/min, or even from 15 ml/min to 20 ml/min. It is envisioned that the flow rate of the hydrogen may be from any of the lower limits disclosed herein to any of the upper limits disclosed herein. Without intending to be bound by any particular theory, it is believed that a hydrogen flow rate into the reactor less than 15 ml/min may not allow sufficient levels of hydrogen into the reactor. However, a hydrogen flow rate greater than 35 ml/min may cause too much hydrogen to circulate within the system, such that an unacceptable amount of the hydrogen is consumed.

In embodiments, the pyrolysis oil, diluent, hydrogen, and mixed metal oxide catalyst are allowed to reside in the slurry-phase reactor 110 for a period of time from 1.5 h to 7.5 h. For example, the components may be allowed to reside in the slurry-phase reactor for from 1.5 h to 7 h, from 1.5 h to 6.5 h, from 1.5 h to 6 h, from 1.5 h to 5.5 h, from 1.5 h to 5 h, from 1.5 h to 4.5 h, from 1.5 h to 4 h, from 1.5 h to 3.5 h, from 1.5 h to 3 h, from 1.5 h to 2.5 h, from 1.5 h to 2 h, from 2 h to 7.5 h, from 2.5 h to 7.5 h, from 3 h to 7.5 h, from 3.5 h to 7.5 h, from 4 h to 7.5 h, from 4.5 h to 7.5 h, from 5 h to 7.5 h, from 5.5 h to 7.5 h, from 6 h to 7.5 h, from 6.5 h to 7.5 h, or even from 7 h to 7.5 h. It is envisioned that the flow rate of the pyrolysis oil and diluent may be from any of the lower limits disclosed herein to any of the upper limits disclosed herein. Without intending to be bound by any particular theory, it is believed that if the components are allowed to reside in the slurry-phase reactor for less than 1.5 h, one or more of the continuous selective hydrogenation, selective opening of saturated rings, hydro-dealkylation, trans-alkylation, and disproportionation may not have sufficient time to proceed to completion. However, unwanted byproducts may be produced if this time is extended beyond 7.5 h.

In embodiments, the slurry-phase reactor 110 may be operated at a temperature from 350° C. to 450° C., such as from 360° C. to 450° C., from 370° C. to 450° C., from 380° C. to 450° C., from 390° C. to 450° C., from 400° C. to 450° C., from 410° C. to 450° C., from 420° C. to 450° C., from 430° C. to 450° C., from 440° C. to 450° C., from 350° C. to 440° C., from 350° C. to 430° C., from 350° C. to 420° C., from 350° C. to 410° C., from 350° C. to 400° C., from 350° C. to 390° C., from 350° C. to 380° C., from 350° C. to 370° C., or even from 350° C. to 360° C. It is envisioned that the temperature may be from any of the lower limits disclosed herein to any of the upper limits disclosed herein. Without intending to be bound by any particular theory, it is believed that having a reactor temperature below 350° C. may cause one or more of the continuous selective hydrogenation, selective opening of saturated rings, hydro-dealkylation, trans-alkylation, and disproportionation to proceed too slowly to be commercially viable, but having a reactor temperature above 450° C. may cause one or more of these reactions to proceed too quickly, which may lead to a runaway reaction or premature deactivation of the catalyst.

In embodiments, the slurry-phase reactor 110 may be operated at a pressure from 3 MPa to 18 MPa, from 3.5 MPa to 18 MPa, from 4 MPa to 18 MPa, from 4.5 MPa to 18 MPa, from 5 MPa to 18 MPa, from 5.5 MPa to 18 MPa, from 6 MPa to 18 MPa, from 6.5 MPa to 18 MPa, from 7 MPa to 18 MPa, from 7.5 MPa to 18 MPa, from 8 MPa to 18 MPa, from 8.5 MPa to 18 MPa, from 9 MPa to 18 MPa, from 9.5 MPa to 18 MPa, from 10 MPa to 18 MPa, from 10.5 MPa to 18 MPa, from 11 MPa to 18 MPa, from 11.5 MPa to 18 MPa, from 12 MPa to 18 MPa, from 12.5 MPa to 18 MPa, from 13 MPa to 18 MPa, from 13.5 MPa to 18 MPa, from 14 MPa to 18 MPa, from 14.5 MPa to 18 MPa, from 15 MPa to 18 MPa, from 15.5 MPa to 18 MPa, from 16 MPa to 18 MPa, from 3 MPa to 17.5 MPa, from 3 MPa to 17 MPa, from 3 MPa to 16.5 MPa, from 3 MPa to 16 MPa, from 3 MPa to 15.5 MPa, from 3 MPa to 15 MPa, from 3 MPa to 14.5 MPa, from 3 MPa to 14 MPa, from 3 MPa to 13.5 MPa, from 3 MPa to 13 MPa, from 3 MPa to 12.5 MPa, from 3 MPa to 12 MPa, from 3 MPa to 11.5 MPa, from 3 MPa to 11 MPa, from 3 MPa to 10.5 MPa, from 3 MPa to 10 MPa, from 3 MPa to 9.5 MPa, from 3 MPa to 9 MPa, from 3 MPa to 8.5 MPa, from 3 MPa to 8 MPa, from 3 MPa to 7.5 MPa, from 3 MPa to 7 MPa, from 3 MPa to 6.5 MPa, from 3 MPa to 6 MPa, from 3 MPa to 5.5 MPa, or even from 3 MPa to 5 MPa. It is envisioned that the pressure may be from any of the lower limits disclosed herein to any of the upper limits disclosed herein. Without intending to bound by any particular theory, it is believed that a pressure below 3 MPa may be insufficient for one or more of the continuous selective hydrogenation, selective opening of saturated rings, hydro-dealkylation, trans-alkylation, and disproportionation to take place. However, at a pressure above 18 MPa, specialized high-pressure equipment may become necessary, which would increase the cost of performing the reaction.

As stated above, the slurry-phase reactor 110 includes a mixed metal oxide catalyst. In embodiments, the mixed metal oxide catalyst comprises two or more of $Fe_2O_3$, $ZrO_2$, $CeO_2$, $Al_2O_3$, $TiO_2$, $MoO_3$, $Co_2O_3$, and NiO. In embodiments, the mixed metal oxide catalyst may include from 70 wt. % to 90 wt. % $Fe_2O_3$; from 5 wt. % to 60 wt. % $ZrO_2$; from 1 wt. % to 4 wt. % $CeO_2$; and from 5 wt. % to 10 wt. % $Al_2O_3$, where wt. % is calculated based on the total amount of oxides. In embodiments, the mixed metal oxide catalyst may include from 10 wt. % to 50 wt. % $TiO_2$; from 10 wt. % to 15 wt. % $MoO_3$; from 1 wt. % to 10 wt. % $Co_2O_3$; and from 1 wt. % to 5 wt. % NiO, where wt. % is calculated based on the total amount of oxides.

In embodiments, from 90% to 100% of the pyrolysis oil may be converted to the intermediate products. For instance from 90% to 99%, from 90% to 98%, from 90% to 97%, from 90% to 96%, from 90% to 95%, from 90% to 94%, from 90% to 93%, from 90% to 92%, from 90% to 91%, from 91% to 100%, from 92% to 100%, from 93% to 100%, from 94% to 100%, from 95% to 100%, from 96% to 100%, from 97% to 100%, from 98% to 100%, or even from 99% to 100% of the pyrolysis oil may be converted to the intermediate products. It is envisioned that the yield of intermediate products may be from any of the lower limits disclosed herein to any of the upper limits disclosed herein.

Referring to FIG. 2, as noted above, the fixed-bed reactor 120 may contain a mesoporous zeolite-supported metal catalyst, which is described in more detail below. The fixed-bed reactor feed 23 may be contacted with the mesoporous zeolite-supported metal catalysts while hydrogen gas 25 is added. Optionally, before being contacted with the mesoporous zeolite-supported metal catalysts, the fixed-bed reactor feed 23 may pass through a heat exchanger (not shown). The optional heat exchanger may help to control the temperature of the liquid intermediate products at a temperature sufficient to avoid condensation of the intermediate products between the slurry-phase reactor 110 and the fixed-bed reactor 120.

After reacting with the mesoporous zeolite-supported metal catalyst in the fixed-bed reactor 120, a separator 150 may remove the pyrolysis gasoline 10 from other components in the fixed-bed reactor 120 effluent, so that the pyrolysis gas may be further upgraded in the aromatization unit 300.

Figure 4:
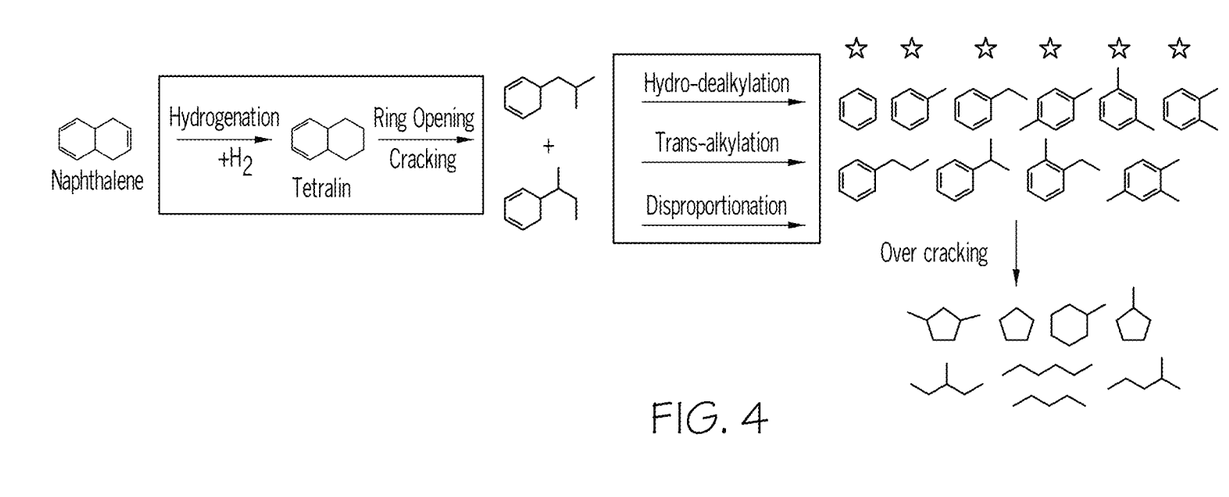
FIG. 4 is a diagram of chemical processes performed in the pyrolysis gasoline upgrading according to one or more embodiments of the present disclosure.

In operation, contacting the intermediates in the fixed-bed reactor 120 with the mesoporous zeolite-supported metal catalysts, described more fully below, produces BTX by selective hydrogenation, selective opening of the saturated ring, and then further hydro-dealkylation, trans-alkylation, and disproportionation. This cascade of reactions is shown in FIG. 4, beginning with naphthalene and resulting in BTX. In the event of over-cracking, saturated hydrocarbons may also be produced. The formation of BTX from naphthalene is, of course, merely an example of the cascade of reactions, and other starting materials are contemplated.

Conditions of the reactor, such as flow rate into the reactor, temperature in the reactor, and pressure in the reactor may be varied to control the reaction in the fixed-bed reactor 120. In embodiments, the flow rate of the hydrogen gas may be from 15 ml/min to 35 ml/min, such as from 20 ml/min to 35 ml/min, from 25 ml/min to 35 ml/min, from 30 ml/min to 35 ml/min, from 15 ml/min to 30 ml/min, from 15 ml/min to 25 ml/min, or even from 15 ml/min to 20 ml/min. It is envisioned that the hydrogen flow rate may be from any of the lower limits disclosed herein to any of the upper limits disclosed herein. Without intending to be bound by any particular theory, it is believed that a hydrogen flow rate into the reactor less than 15 ml/min may not allow sufficient levels of hydrogen into the fixed-bed reactor 120. However, a hydrogen flow rate greater than 35 ml/min may cause too much hydrogen to circulate within the system, such that an unacceptable amount of the hydrogen is consumed.

In embodiments, the flow rate into the fixed-bed reactor 120 may be from 0.2 g/min to 1 g/min, such as from 0.3 g/min to 1 g/min, from 0.4 g/min to 1 g/min, from 0.5 g/min to 1 g/min, from 0.6 g/min to 1 g/min, from 0.7 g/min to 1 g/min, from 0.8 g/min to 1 g/min, from 0.9 g/min to 1 g/min, from 0.2 g/min to 0.9 g/min, from 0.2 g/min to 0.8 g/min, from 0.2 g/min to 0.7 g/min, from 0.2 g/min to 0.6 g/min, from 0.2 g/min to 0.5 g/min, from 0.2 g/min to 0.4 g/min, or even from 0.2 g/min to 0.3 g/min. It is envisioned that the flow rate may be from any of the lower limits disclosed herein to any of the upper limits disclosed herein. Any convenient apparatus for controlling the flow rate, such as a liquid pump, may be used.

In embodiments, the fixed-bed reactor 120 may be operated at a temperature from 350° C. to 450° C., such as from 360° C. to 450° C., from 370° C. to 450° C., from 380° C. to 450° C., from 390° C. to 450° C., from 400° C. to 450° C., from 410° C. to 450° C., from 420° C. to 450° C., from 430° C. to 450° C., from 440° C. to 450° C., from 350° C. to 440° C., from 350° C. to 430° C., from 350° C. to 420° C., from 350° C. to 410° C., from 350° C. to 400° C., from 350° C. to 390° C., from 350° C. to 380° C., from 350° C. to 370° C., or even from 350° C. to 360° C. It is envisioned that the temperature may be from any of the lower limits disclosed herein to any of the upper limits disclosed herein. The temperature within the fixed-bed reactor may be, but need not be, the same as the temperature within the slurry-phase reactor. Without intending to be bound by any particular theory, it is believed that having a reactor temperature below 350° C. may cause one or more of the selective hydrogenation, selective opening of the saturated ring, and then further hydro-dealkylation, trans-alkylation, and disproportionation to proceed too slowly to be commercially viable, but having a reactor temperature above 450° C. may cause one or more of these reactions to proceed too quickly, which may lead to a runaway reaction or premature deactivation of the catalyst.

In embodiments, the fixed-bed reactor 120 may be operated at a pressure from 3 MPa to 18 MPa, from 3.5 MPa to 18 MPa, from 4 MPa to 18 MPa, from 4.5 MPa to 18 MPa, from 5 MPa to 18 MPa, from 5.5 MPa to 18 MPa, from 6 MPa to 18 MPa, from 6.5 MPa to 18 MPa, from 7 MPa to 18 MPa, from 7.5 MPa to 18 MPa, from 8 MPa to 18 MPa, from 8.5 MPa to 18 MPa, from 9 MPa to 18 MPa, from 9.5 MPa to 18 MPa, from 10 MPa to 18 MPa, from 10.5 MPa to 18 MPa, from 11 MPa to 18 MPa, from 11.5 MPa to 18 MPa, from 12 MPa to 18 MPa, from 12.5 MPa to 18 MPa, from 13 MPa to 18 MPa, from 13.5 MPa to 18 MPa, from 14 MPa to 18 MPa, from 14.5 MPa to 18 MPa, from 15 MPa to 18 MPa, from 15.5 MPa to 18 MPa, from 16 MPa to 18 MPa, from 3 MPa to 17.5 MPa, from 3 MPa to 17 MPa, from 3 MPa to 16.5 MPa, from 3 MPa to 16 MPa, from 3 MPa to 15.5 MPa, from 3 MPa to 15 MPa, from 3 MPa to 14.5 MPa, from 3 MPa to 14 MPa, from 3 MPa to 13.5 MPa, from 3 MPa to 13 MPa, from 3 MPa to 12.5 MPa, from 3 MPa to 12 MPa, from 3 MPa to 11.5 MPa, from 3 MPa to 11 MPa, from 3 MPa to 10.5 MPa, from 3 MPa to 10 MPa, from 3 MPa to 9.5 MPa, from 3 MPa to 9 MPa, from 3 MPa to 8.5 MPa, from 3 MPa to 8 MPa, from 3 MPa to 7.5 MPa, from 3 MPa to 7 MPa, from 3 MPa to 6.5 MPa, from 3 MPa to 6 MPa, from 3 MPa to 5.5 MPa, or even from 3 MPa to 5 MPa. It is envisioned that the pressure may be from any of the lower limits disclosed herein to any of the upper limits disclosed herein. Without intending to bound by any particular theory, it is believed that a pressure below 3 MPa may be insufficient for one or more of the selective hydrogenation, selective opening of the saturated ring, and then further hydro-dealkylation, trans-alkylation, and disproportionation to take place. However, at a pressure above 18 MPa, specialized high-pressure equipment may become necessary, which would increase the cost of performing the reaction.

The fixed-bed reactor 120 includes a mesoporous zeolite-supported metal catalyst. Generally, zeolites may be characterized by a framework type, which defines their microporous structure. The zeolites described presently, in one or more embodiments, are not particularly limited by framework type. Framework types are described in, for example, "Atlas of Zeolite Framework Types" by Ch. Baerlocher et al, Fifth Revised Edition, 2001, which is incorporated by reference herein. In embodiments, the zeolites may comprise microstructures (which include micropores) characterized as, among others, *BEA framework type zeolites (such as, but not limited to, zeolite Beta), FAU framework type zeolites (such as, but not limited to, zeolite Y), MOR framework type zeolites, or MFI framework type zeolite (such as, but not limited to, ZSM-5). It should be understood that *BEA, MFI, MOR, and FAU refer to zeolite framework types as identified by their respective three letter codes established by the International Zeolite Association (IZA). Other framework types are contemplated in the presently disclosed embodiments. In embodiments, the mesoporous zeolite of the catalyst may be zeolite Beta, ZSM-5, Mordenite, Zeolite Y, and combinations of two or more thereof. The metal of the catalyst may be derived from a heteropolyacid. Exemplary heteropolyacids include Keggin-type heteropolyacids, such as one or more of phosphortungstic heteropolyacid ($H_3PW_{12}O_{40}$), phosphormolybdic heteropolyacid ($H_3PMo_{12}O_{40}$), silicotungstic heteropolyacid ($H_4SiW_{12}O_{40}$), silicomolybdic heteropolyacid ($H_4SiMo_{12}O_{40}$).

Referring to FIG. 2, the pyrolysis gasoline 10 is then aromatized in an aromatization unit 300. In a further embodiment, the pyrolysis gas 7 from a steam cracker 100 may also be fed to the aromatization unit 300 to further the aromatic yield.

An exemplary pygas formulation may include from 15 weight % ("wt %") to 20 wt % paraffins; from 1.5 wt % to 3 wt % naphthenes; from 50 wt % to 70 wt % aromatic hydrocarbons; from 1 wt % to 2 wt % di-aromatic hydrocarbons; from 5 wt % to 10 wt % olefins; and from 7 wt % to 9 wt % di-olefins. In embodiments, the sum of the concentration of each of the above components of pygas is about 100 wt %, such as from 99.5 wt % to 100.5 wt %, which allows for the presence of impurities and experimental variation.

In the aromatization unit 300, the paraffins are converted, at least partially, to BTX by undergoing cyclization, dealkylation, and/or hydrodealkylation reactions. In embodiments, the aromatizing may include contacting the hydrotreated pyrolysis gasoline stream with a catalyst comprising a zeolite. In embodiments, the zeolite may include a Y-type zeolite, a ZSM-5-type zeolite, or a combination of the Y-type zeolite and the ZSM-5-type zeolite. In embodiments, a single reactor may be used for all of cyclization, dealkylation, and hydrodealkylation. In other embodiments, more than one reactor, such as two reactors, may be used to perform cyclization, dealkylation, and hydrodealkylation. For instance, one reactor may be used for cyclization and another reactor may be used for dealkylation and/or hydrodealkylation. In embodiments using more than one reactor, the catalyst may be the same or different in each reactor. Further, the temperature, pressure, and WHSV may all be the same or different in each reactor.

In embodiments, the aromatization unit 300 may be operated at a temperature from 200° C. to 700° C., from 200° C. to 650° C., from 200° C. to 600° C., from 200° C. to 550° C., from 200° C. to 500° C., from 200° C. to 450° C., from 200° C. to 400° C., from 200° C. to 350° C., from 200° C. to 300° C., from 200° C. to 250° C., from 250° C. to 700° C., from 300° C. to 950° C., from 350° C. to 700° C., from 400° C. to 700° C., from 450° C. to 700° C., from 450° C. to 650° C., from 500° C. to 700° C., from 500° C. to 600° C., from 525° C. to 575° C., from 550° C. to 700° C., from 600° C. to 700° C., or even from 650° C. to 700° C. It should be understood that the temperature may be from any lower bound for such temperature disclosed herein to any upper bound for such temperature disclosed herein. Without intending to be bound by any particular theory, it is believed that having a reactor temperature below 200° C. may cause the cyclization, dealkylation, and/or hydrodealkylation reactions to proceed too slowly to be commercially viable, but having a reactor temperature above 700° C. may cause polymerization of species found in the reactor, thereby coking the catalyst.

In embodiments, the aromatization unit 300 may be operated at a pressure from 0.1 MPa to 3 MPa, from 0.1 MPa to 2.9 MPa, from 0.1 MPa to 2.8 MPa, from 0.1 MPa to 2.7 MPa, from 0.1 MPa to 2.6 MPa, from 0.1 MPa to 2.5 MPa, from 0.1 MPa to 2.4 MPa, from 0.1 MPa to 2.3 MPa, from 0.1 MPa to 2.2 MPa, from 0.1 MPa to 2.1 MPa, from 0.1 MPa to 2 MPa, from 0.1 MPa to 1.9 MPa, from 0.1 MPa to 1.8 MPa, from 0.1 MPa to 1.7 MPa, from 0.1 MPa to 1.6 MPa, from 0.1 MPa to 1.5 MPa, from 0.1 MPa to 1.4 MPa, from 0.1 MPa to 1.3 MPa, from 0.1 MPa to 1.2 MPa, from 0.1 MPa to 1.1 MPa, from 0.1 MPa to 1 MPa, from 0.1 MPa to 0.9 MPa, from 0.1 MPa to 0.8 MPa, from 0.1 MPa to 0.7 MPa, from 0.1 MPa to 0.6 MPa, from 0.1 MPa to 0.5 MPa, from 0.1 MPa to 0.4 MPa, from 0.1 MPa to 0.3 MPa, from 0.1 MPa to 0.2 MPa, from 0.2 MPa to 3 MPa, from 0.3 MPa to 3 MPa, from 0.4 MPa to 3 MPa, from 0.5 MPa to 3 MPa, from 0.6 MPa to 3 MPa, from 0.7 MPa to 3 MPa, from 0.8 MPa to 3 MPa, from 0.9 MPa to 3 MPa, from 1 MPa to 3 MPa, from 1.1 MPa to 3 MPa, from 1.2 MPa to 3 MPa, from 1.3 MPa to 3 MPa, from 1.4 MPa to 3 MPa, from 1.5 MPa to 3 MPa, from 1.6 MPa to 3 MPa, from 1.7 MPa to 3 MPa, from 1.8 MPa to 3 MPa, from 1.9 MPa to 3 MPa, from 2 MPa to 3 MPa, from 2.1 MPa to 3 MPa, from 2.2 MPa to 3 MPa, from 2.3 MPa to 3 MPa, from 2.4 MPa to 3 MPa, from 2.5 MPa to 3 MPa, from 2.6 MPa to 3 MPa, from 2.7 MPa to 3 MPa, from 2.8 MPa to 3 MPa, or even from 2.9 MPa to 3 MPa. It should be understood that the operating pressure may be from any lower bound for such pressure disclosed herein to any upper bound for such pressure disclosed herein. Without intending to be bound by any particular theory, it is believed that a pressure below 0.1 MPa may be insufficient for the cyclization, dealkylation, and/or hydrodealkylation to take place. However, at a pressure above 3 MPa, specialized high-pressure equipment may become necessary, which would increase the cost of performing the reaction.

In embodiments, the aromatization unit 300 may be operated at a WHSV from $0.1\ h^{-1}$ to $20\ h^{-1}$, from $0.1\ h^{-1}$ to $19\ h^{-1}$, from $0.1\ h^{-1}$ to $18\ h^{-1}$, from $0.1\ h^{-1}$ to $17\ h^{-1}$, from $0.1\ h^{-1}$ to $16\ h^{-1}$, from $0.1\ h^{-1}$ to $15\ h^{-1}$, from $0.1\ h^{-1}$ to $14\ h^{-1}$, from $0.1\ h^{-1}$ to $13\ h^{-1}$, from $0.1\ h^{-1}$ to $12\ h^{-1}$, from $0.1\ h^{-1}$ to $11\ h^{-1}$, from $0.1\ h^{-1}$ to $10\ h^{-1}$, from $0.1\ h^{-1}$ to $9\ h^{-1}$, from $0.1\ h^{-1}$ to $8\ h^{-1}$, from $0.1\ h^{-1}$ to $7\ h^{-1}$, from $0.1\ h^{-1}$ to $6\ h^{-1}$, from $0.1\ h^{-1}$ to $5\ h^{-1}$, from $0.1\ h^{-1}$ to $4\ h^{-1}$, from $0.1\ h^{-1}$ to $3\ h^{-1}$, from $0.1\ h^{-1}$ to $2\ h^{-1}$, from $0.1\ h^{-1}$ to $1\ h^{-1}$, from $0.5\ h^{-1}$ to $5\ h^{-1}$, from $0.75\ h^{-1}$ to $1.25\ h^{-1}$, from $1\ h^{-1}$ to $20\ h^{-1}$, from $2\ h^{-1}$ to $20\ h^{-1}$, from $3\ h^{-1}$ to $20\ h^{-1}$, from $4\ h^{-1}$ to $20\ h^{-1}$, from $5\ h^{-1}$ to $20\ h^{-1}$, from $6\ h^{-1}$ to $20\ h^{-1}$, from $7\ h^{-1}$ to $20\ h^{-1}$, from $8\ h^{-1}$ to $20\ h^{-1}$, from $9\ h^{-1}$ to $20\ h^{-1}$, from $10\ h^{-1}$ to $20\ h^{-1}$, from $11\ h^{-1}$ to $20\ h^{-1}$, from $12\ h^{-1}$ to $20\ h^{-1}$, from $13\ h^{-1}$ to $20\ h^{-1}$, from $14\ h^{-1}$ to $20\ h^{-1}$, from $15\ h^{-1}$ to $20\ h^{-1}$, from $16\ h^{-1}$ to $20\ h^{-1}$, from $17\ h^{-1}$ to $20\ h^{-1}$, from $18\ h^{-1}$ to $20\ h^{-1}$, or even from $19\ h^{-1}$ to $20\ h^{-1}$. It should be understood that the WHSV may be from any lower bound for such WHSV disclosed herein to any upper bound for such WHSV disclosed herein. Without intending to be bound by any particular theory, it is believed that a WHSV below $0.1\ h^{-1}$ may require a catalyst volume and/or reactor volume that is too large to be commercially viable, or a higher residence time of the reactants may be necessary, thereby leading to a decreased amount of time to catalyst deactivation. However, a WHSV above $20\ h^{-1}$ may cause a residence time of the reactants in the reactor that is too short to allow the hydrogenation to proceed.

Referring to FIGS. 1 and 2, after aromatization, the product 13 from the aromatization unit 300 is hydrodealkylated and transalkylated a in a hydrodealkylation-transalkylation unit 400 to produce an aromatic stream 16.

In embodiments, the hydrodealkylation-transalkylation 400 may be a fixed-bed reactor. The fixed bed reactor may be charged with a catalyst composition that includes an active metal supported on a mesoporous zeolite. The active metal may be, for example, nickel, molybdenum, tungsten, platinum, palladium, or a mixture of two or more of these. The support may be, for example, a mesoporous zeolite such as beta mordenite or ZSM-5.

In embodiments, the hydrodealkylation-transalkylation unit 400 may be operated at a temperature from 300° C. to 500° C., such as from 300° C. to 490° C., from 300° C. to 480° C., from 300° C. to 470° C., from 300° C. to 460° C., from 300° C. to 450° C., from 300° C. to 440° C., from 300° C. to 430° C., from 300° C. to 420° C., from 300° C. to 410° C., from 300° C. to 400° C., from 300° C. to 390° C., from 300° C. to 380° C., from 300° C. to 370° C., from 300° C. to 360° C., from 300° C. to 350° C., from 300° C. to 340° C., from 300° C. to 330° C., from 300° C. to 320° C., from 300° C. to 310° C., from 310° C. to 500° C., from 320° C. to 500° C., from 330° C. to 500° C., from 340° C. to 500° C., from 350° C. to 500° C., from 360° C. to 500° C., from 370° C. to 500° C., from 380° C. to 500° C., from 380° C. to 480° C., from 390° C. to 500° C., from 400° C. to 500° C., from 410° C. to 500° C., from 420° C. to 500° C., from 430° C. to 500° C., from 440° C. to 500° C., from 450° C. to 500° C., from 460° C. to 500° C., from 470° C. to 500° C., from 480° C. to 500° C., or even from 490° C. to 500° C. It should be understood that the temperature may be from any lower bound for such temperature disclosed herein to any upper bound for such temperature disclosed herein. Without intending to be bound by any particular theory, it is believed that having a reactor temperature below 300° C. may cause the hydrodealkylation and transalkylation reactions to proceed too slowly to be commercially viable, but having a reactor temperature above 500° C. may cause an increase in undesirable byproducts, thereby decreasing the effectiveness of this stage.

In embodiments, the hydrodealkylation-transalkylation reactor 400 may be operated at a pressure from 1.5 MPa to 6 MPa, such as from 1.5 MPa to 5.9 MPa, from 1.5 MPa to 5.8 MPa, from 1.5 MPa to 5.7 MPa, from 1.5 MPa to 5.6 MPa, from 1.5 MPa to 5.5 MPa, from 1.5 MPa to 5.4 MPa, from 1.5 MPa to 5.3 MPa, from 1.5 MPa to 5.2 MPa, from 1.5 MPa to 5.1 MPa, from 1.5 MPa to 5 MPa, from 1.5 MPa to 4.9 MPa, from 1.5 MPa to 4.8 MPa, from 1.5 MPa to 4.7 MPa, from 1.5 MPa to 4.6 MPa, from 1.5 MPa to 4.5 MPa, from 1.5 MPa to 4.4 MPa, from 1.5 MPa to 4.3 MPa, from 1.5 MPa to 4.2 MPa, from 1.5 MPa to 4.1 MPa, from 1.5 MPa to 4 MPa, from 1.5 MPa to 3.9 MPa, from 1.5 MPa to 3.8 MPa, from 1.5 MPa to 3.7 MPa, from 1.5 MPa to 3.6 MPa, from 1.5 MPa to 3.5 MPa, from 1.5 MPa to 3.4 MPa, from 1.5 MPa to 3.3 MPa, from 1.5 MPa to 3.2 MPa, from 1.5 MPa to 3.1 MPa, from 1.5 MPa to 3 MPa, from 1.5 MPa to 2.9 MPa, from 1.5 MPa to 2.8 MPa, from 1.5 MPa to 2.7 MPa, from 1.5 MPa to 2.6 MPa, from 1.5 MPa to 2.5 MPa, from 1.5 MPa to 2.4 MPa, from 1.5 MPa to 2.3 MPa, from 1.5 MPa to 2.2 MPa, from 1.5 MPa to 2.1 MPa, from 1.5 MPa to 2 MPa, from 1.5 MPa to 1.9 MPa, from 1.5 MPa to 1.8 MPa, from 1.5 MPa to 1.7 MPa, from 1.5 MPa to 1.6 MPa, from 1.6 MPa to 6 MPa, from 1.7 MPa to 6 MPa, from 1.8 MPa to 6 MPa, from 1.9 MPa to 6 MPa, from 2 MPa to 6 MPa, from 2.1 MPa to 6 MPa, from 2.2 MPa to 6 MPa, from 2.3 MPa to 6 MPa, from 2.4 MPa to 6 MPa, from 2.5 MPa to 6 MPa, from 2.6 MPa to 6 MPa, from 2.7 MPa to 6 MPa, from 2.8 MPa to 6 MPa, from 2.9 MPa to 6 MPa, from 3 MPa to 6 MPa, from 3.1 MPa to 6 MPa, from 3.2 MPa to 6 MPa, from 3.3 MPa to 6 MPa, from 3.4 MPa to 6 MPa, from 3.5 MPa to 6 MPa, from 3.6 MPa to 6 MPa, from 3.7 MPa to 6 MPa, from 3.8 MPa to 6 MPa, from 3.9 MPa to 6 MPa, from 4 MPa to 6 MPa, from 4.1 MPa to 6 MPa, from 4.2 MPa to 6 MPa, from 4.3 MPa to 6 MPa, from 4.4 MPa to 6 MPa, from 4.5 MPa to 6 MPa, from 4.6 MPa to 6 MPa, from 4.7 MPa to 6 MPa, from 4.8 MPa to 6 MPa, from 4.9 MPa to 6 MPa, from 5 MPa to 6 MPa, from 5.1 MPa to 6 MPa, from 5.2 MPa to 6 MPa, from 5.3 MPa to 6 MPa, from 5.4 MPa to 6 MPa, from 5.5 MPa to 6 MPa, from 5.6 MPa to 6 MPa, from 5.7 MPa to 6 MPa, from 5.8 MPa to 6 MPa, or even from 5.9 MPa to 6 MPa. It should be understood that the pressure of the hydrodealkylation-transalkylation unit 400 may be from any lower bound for such pressure disclosed herein to any upper bound for such pressure disclosed herein. Without intending to be bound by any particular theory, it is believed that a pressure below 1.5 MPa may be insufficient for the hydrodealkylation and/or transalkylation to take place. However, at a pressure above 6 MPa, specialized high-pressure equipment may become necessary, which would increase the cost of performing the reaction.

Referring again to FIGS. 1 and 2, the aromatic stream 16 which is produced in the hydrodealkylation-transalkylation unit 400 is then processed in an aromatics recovery complex (ARC) 500 to produce aromatic compounds comprising benzene 18, toluene 19, and xylenes 20 (BTX). Raffinate 17 may be removed from the top of the ARC 500. Heavy Aromatics ($C_9/C_9+$) 21 may be removed from the bottom of the ARC 500. In further embodiments as shown in FIG. 1, at least a portion of the heavy aromatics steam comprising $C_9$ aromatics or greater may be recycled (see stream 22) from the ARC 500 to the hydrodealkylation-transalkylation unit 400. Additionally, there may be a separator 410 upstream of the ARC 500 to remove some lighter carbon components prior to being fed to the ARC 500.

Within the ARC 500, several processing steps may be conducted in order to recover high value products, e.g., xylenes and benzene, and to convert lower value products, e.g., toluene, into higher value products. For example, the aromatics present may be separated into different fractions by carbon number; e.g. benzene, toluene, xylenes, and ethylbenzene, etc. The $C_8$ fraction may then be subjected to a processing scheme to prepare para-xylene ("p-xylene"), which is a high value product. P-xylene may be recovered in high purity from the $C_8$ fraction by separating the p-xylene from the ortho-xylene ("o-xylene"), meta-xylene ("m-xylene"), and ethylbenzene using selective adsorption or crystallization. The o-xylene and m-xylene remaining from the p-xylene separation may be isomerized to produce an equilibrium mixture of xylenes. The ethylbenzene may be isomerized into xylenes or dealkylated to benzene and ethane. The p-xylene of the equilibrium mixture may also be separated from the o-xylene and the m-xylene using adsorption or crystallization, and the p-xylene-depleted stream may be recycled to the isomerization unit and then to the p-xylene recovery unit until all of the o-xylene and m-xylene are converted to p-xylene and recovered, or at least until it is no longer economically feasible to attempt to convert additional p-xylene.

EXAMPLES

Using embodiments described above, an exemplary upgrading system and process was simulated using the HYSIS v 10.0 simulator, as follows. The following examples are merely illustrative and should not be interpreted as limiting the scope of the present disclosure.

Comparative Process

Figure 5:
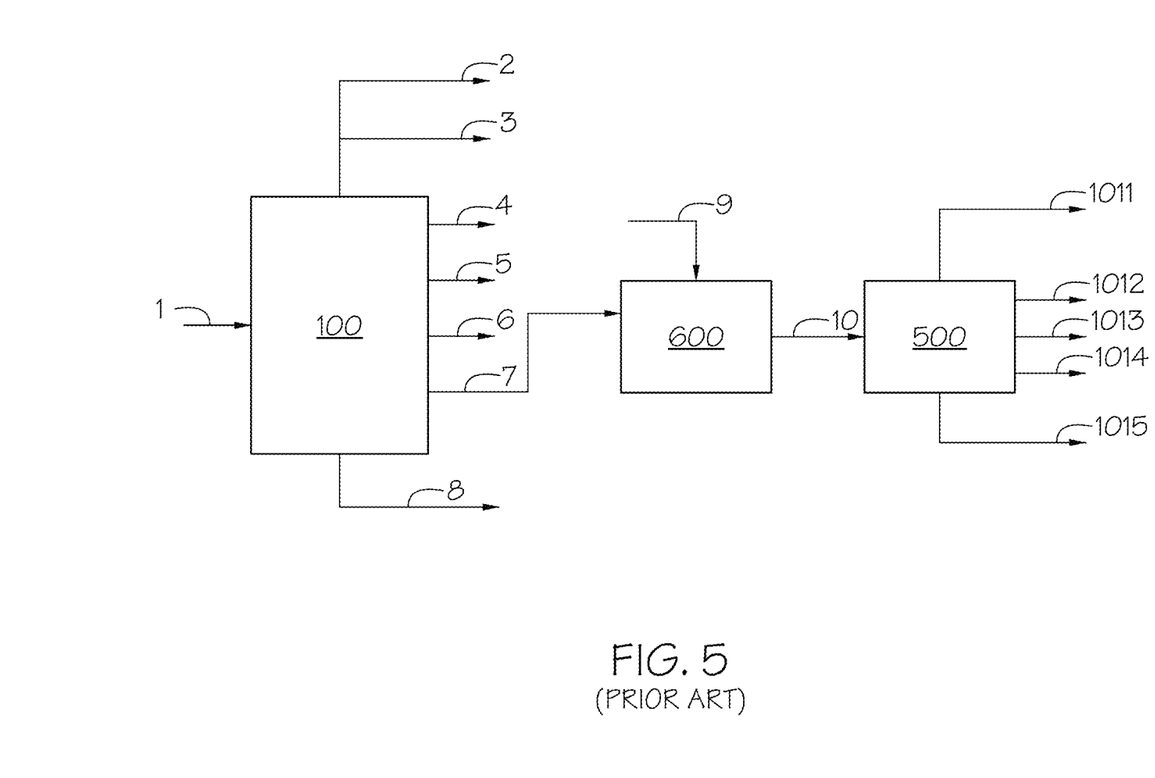

Referring to FIG. 5, a process flow diagram of a conventional process is shown. In this configuration, pyrolysis gasoline is hydrotreated to remove di and mono olefins, which are detrimental to the adsorbents used in xylene separation, and then deoleifinized stream is sent to the aromatic recovery complex. Additionally, pyrolysis oil is not converted to pyrolysis gasoline; rather it is just discarded. 380° C., 30 bar, WHSV 1.2 $h^{-1}$ The material balance for that process configuration is provided in Table 1 as follows.

TABLE 1

| Material Balance for Prior Art FIG. 5 | | | | | | | | | |
|---|---|---|---|---|---|---|---|---|---|
| Stream# | 7 | 8 | 9 | 10 | 1011 | 1012 | 1013 | 1014 | 1015 |
| Flowrate. Kg/hr | 500 | 100 | 2.5 | 502.5 | 190.4 | 171.3 | 69.1 | 19.0 | 52.6 |
| Composition, wt % | | | | | | | | | |
| $H_2$ | | | | 100% | 0.3% | 0.9% | | | |
| (C1-C4) | | | | | | | | | |
| C5+ non-aromatic | | | | | 37.5% | 99.1% | | | |

TABLE 1-continued

Material Balance for Prior Art FIG. 5

| Stream# | 7 | 8 | 9 | 10 | 1011 | 1012 | 1013 | 1014 | 1015 |
|---|---|---|---|---|---|---|---|---|---|
| Benzene | | | | 34.1% | 100% | | | | |
| Toluene | | | | 13.8% | | 100% | | | |
| EB | | | | 1.3% | | | | 34.2% | |
| Xylene | | | | 2.5% | | | | 65.8% | |
| C9+ Aromatics | | | | 10.5% | | | | | 100% |
| Pygas | 100% | | | | | | | | |
| Pyoil | | 100% | | | | | | | |
| Fuel Gas | | | | | | | | | |
| Fuel Oil | | | | | | | | | |
| Total | 100% | 100% | 100% | 100% | 100% | 100% | 100% | 100% | 100% |

Inventive Example

For the Process of FIG. 1, Table 2 includes the process conditions and Table 3 includes the material balance.

TABLE 2

Process Conditions for Process of FIG. 1.

| Reactor Number | Reactor type | Reaction conditions | Catalyst |
|---|---|---|---|
| 110 | Slurry phase reactor | Temp.: 400° C. 140 bar pressure Retention time: 4 hours | Mixed metal oxide catalyst $ZrO_2$—$CeO_2$—$Al_2O_3$—$FeO_x$ |
| 120 | Fixed-bed Reactor | Temp.: 400° C. $H_2$ pressure during reaction: 30-bar WHSV: 1.2 $h^{-1}$ | Zeolite supported metal catalyst CoMoP/Beta |
| 300 | Fixed-bed Aromatization Unit | Temp.: 450-650° C. $H_2$ pressure during reaction: 1-10 bar WHSV: 0.5-5 $h^{-1}$ | Metal modified zeolite catalyst |
| 400 | Fixed-bed Hydrodealkylation/ transalkyation unit | Temp.: 300-450° C. $H_2$ pressure during reaction: 20-50 bar LHSV: 0.5-5 $h^{-1}$ | Zeolite catalyst- Mordenite & Medium pore ZSM-5 |

TABLE 3

Material Balance of FIG. 1

| Stream# | 7 | 8 | 9 | 10 | 11 | 12 | 13 | 14 |
|---|---|---|---|---|---|---|---|---|
| Flowrate. Kg/hr | 500 | 100 | 1.2 | 94.2 | 1.4 | 4.4 | 594.2 | 1.9 |
| Composition, wt % | | | | | | | | |
| H2 | | | 100% | | | | 0% | 100% |
| (C1-C4) | | | | | | | 9% | |
| C5+ non-aromatic | | | | | | | 5% | |
| Benzene | | | | 9.4% | | | 35% | |
| Toluene | | | | 38.2% | | | 28% | |
| EB | | | | | | | 1% | |
| Xylene | | | | 17.3% | | | 5% | |
| C9+ Aromatics | | | | 35.0% | | | 16% | |
| Pygas | 100% | | | | | | | |
| Pyoil | | 100% | | | | | | |
| Fuel Gas | | | | | | 100% | | |
| Fuel Oil | | | | | | | 100% | |
| Total | 100% | 100% | 100% | 100% | 100% | 100% | 100% | 100% |

| Stream# | 15 | 16 | 17 | 18 | 19 | 20 | 21 | 22 |
|---|---|---|---|---|---|---|---|---|
| Flowrate. Kg/hr | 62.9 | 533.2 | 32.5 | 279.1 | 0 | 159.9 | 58.1 | 0 |
| Composition, wt % | | | | | | | | |
| H2 | 3.4% | | | | | | | |
| (C1-C4) | 96.6% | | | | | | | |
| C5+ non-aromatic | | 6.1% | 100% | | | | | |
| Benzene | | 41.1% | | 100% | | | | |
| Toluene | | 22.1% | | | | | | |
| EB | | 2.5% | | | | | | |

TABLE 3-continued

| Material Balance of FIG. 1 | | | | | | | | |
|---|---|---|---|---|---|---|---|---|
| Xylene | | 17.3% | | | 100% | | | |
| C9+ Aromatics | | 10.9% | | | | 100% | | |
| Pygas | | | | | | | | |
| Pyoil | | | | | | | | |
| Fuel Gas | | | | | | | | |
| Fuel Oil | | | | | | | | |
| Total | 100% | 100% | 100% | 100% | 0% | 100% | 100% | 0% |

Stream numbers are shown in FIG. 1 and FIG. 5. Referring to Table 1 and FIG. 5, a 500 Kg/hr pygas feedstream and 100 Kg/hr pyoil will produce about 259 Kg/hr of BTX. In contrast, referring to Table 3 and FIG. 1, the addition of the pyrolysis oil to pyrolysis gas upgrading, pygas aromatization, and hydrodealkylation/transalkylation increased BTX capacity to 439 Kg/hr.

According to an aspect, either alone or in combination with any other aspect, a method for method for producing aromatic compounds from pyrolysis oil comprises: upgrading the pyrolysis oil to pyrolysis gasoline in a multi-stage reactor comprising a slurry-phase reactor and a fixed-bed reactor, wherein the slurry-phase reactor comprises a mixed metal oxide catalyst, and the fixed-bed reactor comprises a mesoporous zeolite-supported metal catalyst; aromatizing the pyrolysis gasoline in an aromatization unit; hydrodealkylating and transalkylating a product from the aromatization unit in a hydrodealkylation-transalkylation unit, thereby producing an aromatic stream; and processing the aromatic stream in an aromatics recovery complex to produce the aromatic compounds comprising benzene, toluene, and xylenes (BTX).

According to a second aspect, either alone or in combination with any of the other aspects, the method further comprises feeding pyrolysis gas from a steam cracker to the aromatization unit.

According to a third aspect, either alone or in combination with any of the other aspects, the pyrolysis oil is from a bottoms product of a steam cracker.

According to a fourth aspect, either alone or in combination with any of the other aspects, the method further comprises recycling a heavy aromatics steam comprising $C_9$ aromatics or greater from the aromatics recovery complex to the hydrodealkylation-transalkylation unit.

According to a fifth aspect, either alone or in combination with any of the other aspects, the aromatizing step comprises one or more of cyclization, dealkylation, and hydrodealkylation reactions.

According to a sixth aspect, either alone or in combination with any of the other aspects, the aromatizing is performed in a reactor having a temperature from 200° C. to 700° C., a weight hour space velocity from 0.1 $h^{-1}$ to 20 $h^{-1}$, and a pressure from 0.1 MPa to 3 MPa.

According to a seventh aspect, either alone or in combination with any of the other aspects, the aromatizing comprises contacting the pyrolysis gasoline with a catalyst comprising a Y-type zeolite, a ZSM-5-type zeolite, or a combination of the Y-type zeolite and the ZSM-5-type zeolite.

According to an eighth aspect, either alone or in combination with any of the other aspects, the slurry-phase reactor is operated at a temperature from 350° C. to 450° C., and a pressure from 3 MPa to 18 MPa.

According to a ninth aspect, either alone or in combination with any of the other aspects, the mixed metal oxide catalyst comprises two or more of $Fe_2O_3$, $ZrO_2$, $CeO_2$, $Al_2O_3$, $TiO_2$, $MoO_3$, $Co_2O_3$, and NiO.

According to a tenth aspect, either alone or in combination with any of the other aspects, the mixed metal oxide catalyst comprises: from 70 wt. % to 90 wt. % $Fe_2O_3$; from 5 wt. % to 60 wt. % $ZrO_2$; from 1 wt. % to 4 wt. % $CeO_2$; and from 5 wt. % to 10 wt. % $Al_2O_3$, where wt. % is calculated based on the total amount of oxides.

According to an eleventh aspect, either alone or in combination with any of the other aspects, the mixed metal oxide catalyst comprises: from 10 wt. % to 50 wt. % $TiO_2$; from 10 wt. % to 15 wt. % $MoO_3$; from 1 wt. % to 10 wt. % $Co_2O_3$; and from 1 wt. % to 5 wt. % NiO, where wt. % is calculated based on the total amount of oxides.

According to an twelfth aspect, either alone or in combination with any of the other aspects, the fixed-bed reactor is operated at a temperature from 350° C. to 450° C., and a pressure from 3 MPa to 18 MPa.

According to a thirteenth aspect, either alone or in combination with any of the other aspects, the metal of the mesoporous zeolite-supported metal catalyst comprises a heteropolyacid.

According to a fourteenth aspect, either alone or in combination with any of the other aspects, the heteropolyacid comprises at least one Keggin-type heteropolyacid selected from the group consisting of phosphortungstic heteropolyacid ($H_3PW_{12}O_{40}$), phosphormolybdic heteropolyacid ($H_3PMo_{12}O_{40}$), silicotungstic heteropolyacid ($H_4SiW_{12}O_{40}$), silicomolybdic heteropolyacid ($H_4SiMo_{12}O_{40}$), and combinations thereof.

According to a fifteenth aspect, either alone or in combination with any of the other aspects, wherein the zeolite support comprises a zeolite selected from the group consisting of zeolite Beta, ZSM-5, Mordenite, Zeolite Y, and combinations of two or more thereof.

It is noted that recitations in the present disclosure of a component of the present disclosure being "operable" or "sufficient" in a particular way, to embody a particular property, or to function in a particular manner, are structural recitations, as opposed to recitations of intended use. More specifically, the references in the present disclosure to the manner in which a component is "operable" or "sufficient" denotes an existing physical condition of the component and, as such, is to be taken as a definite recitation of the structural characteristics of the component.

Having described the subject matter of the present disclosure in detail and by reference to specific embodiments, it is noted that the various details disclosed in the present disclosure should not be taken to imply that these details relate to elements that are essential components of the various embodiments described in the present disclosure. Further, it will be apparent that modifications and variations are possible without departing from the scope of the present disclosure, including, but not limited to, embodiments defined in the appended claims.

The singular forms "a", "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned.

As used in this disclosure and in the appended claims, the words "comprise," "has," and "include" and all grammatical variations thereof are each intended to have an open, non-limiting meaning that does not exclude additional elements or steps.

As used in this disclosure, terms such as "first" and "second" are arbitrarily assigned and are merely intended to differentiate between two or more instances or components. It is to be understood that the words "first" and "second" serve no other purpose and are not part of the name or description of the component, nor do they necessarily define a relative location, position, or order of the component. Furthermore, it is to be understood that the mere use of the term "first" and "second" does not require that there be any "third" component, although that possibility is contemplated under the scope of the present disclosure.

What is claimed is:

1. A method for producing aromatic compounds from pyrolysis oil, the method comprising:
    upgrading the pyrolysis oil to pyrolysis gasoline in a multi-stage reactor comprising a slurry-phase reactor and a fixed-bed reactor, wherein the slurry-phase reactor comprises a mixed metal oxide catalyst, and the fixed-bed reactor comprises a mesoporous zeolite-supported metal catalyst;
    aromatizing the pyrolysis gasoline in an aromatization unit;
    hydrodealkylating and transalkylating a product from the aromatization unit in a hydrodealkylation-transalkylation unit, thereby producing an aromatic stream; and
    processing the aromatic stream in an aromatics recovery complex to produce the aromatic compounds comprising benzene, toluene, and xylenes (BTX).

2. The method of claim 1, further comprising feeding pyrolysis gas from a steam cracker to the aromatization unit.

3. The method of claim 1, wherein the pyrolysis oil is from a bottoms product of a steam cracker.

4. The method of claim 1, further comprising recycling a heavy aromatics steam comprising $C_9$ aromatics or greater from the aromatics recovery complex to the hydrodealkylation-transalkylation unit.

5. The method of claim 1, wherein the aromatizing step comprises one or more of cyclization, dealkylation, and hydrodealkylation reactions.

6. The method of claim 1, wherein the aromatizing is performed in a reactor having a temperature from 200° C. to 700° C., a weight hour space velocity from $0.1\ h^{-1}$ to $20\ h^{-1}$, and a pressure from 0.1 MPa to 3 MPa.

7. The method of claim 1, wherein the aromatizing comprises contacting the pyrolysis gasoline with a catalyst comprising a Y-type zeolite, a ZSM-5-type zeolite, or a combination of the Y-type zeolite and the ZSM-5-type zeolite.

8. The method of claim 1, wherein the slurry-phase reactor is operated at a temperature from 350° C. to 450° C., and a pressure from 3 MPa to 18 MPa.

9. The method of claim 1, wherein the mixed metal oxide catalyst comprises two or more of $Fe_2O_3$, $ZrO_2$, $CeO_2$, $Al_2O_3$, $TiO_2$, $MoO_3$, $Co_2O_3$, and NiO.

10. The method of claim 1, wherein the mixed metal oxide catalyst comprises:
    from 70 wt. % to 90 wt. % $Fe_2O_3$;
    from 5 wt. % to 60 wt. % $ZrO_2$;
    from 1 wt. % to 4 wt. % $CeO_2$; and
    from 5 wt. % to 10 wt. % $Al_2O_3$,
where wt. % is calculated based on the total amount of oxides.

11. The method of claim 1, wherein the mixed metal oxide catalyst comprises:
    from 10 wt. % to 50 wt. % $TiO_2$;
    from 10 wt. % to 15 wt. % $MoO_3$;
    from 1 wt. % to 10 wt. % $Co_2O_3$; and
    from 1 wt. % to 5 wt. % NiO,
where wt. % is calculated based on the total amount of oxides.

12. The method of claim 1, wherein the fixed-bed reactor is operated at a temperature from 350° C. to 450° C., and a pressure from 3 MPa to 18 MPa.

13. The method of claim 1, wherein the metal of the mesoporous zeolite-supported metal catalyst comprises a heteropolyacid.

14. The method of claim 13, wherein the heteropolyacid comprises at least one Keggin-type heteropolyacid selected from the group consisting of phosphortungstic heteropolyacid ($H_3PW_{12}O_{40}$), phosphormolybdic heteropolyacid ($H_3PMo_{12}O_{40}$), silicotungstic heteropolyacid ($H_4SiW_{12}O_{40}$), silicomolybdic heteropolyacid ($H_4SiMo_{12}O_{40}$), and combinations thereof.

15. The method of claim 1, wherein the zeolite support comprises a zeolite selected from the group consisting of zeolite Beta, ZSM-5, Mordenite, Zeolite Y, and combinations of two or more thereof.

* * * * *

UNITED STATES PATENT AND TRADEMARK OFFICE
CERTIFICATE OF CORRECTION

| | |
|---|---|
| PATENT NO. | : 11,732,202 B1 |
| APPLICATION NO. | : 17/703381 |
| DATED | : August 22, 2023 |
| INVENTOR(S) | : Miao Sun et al. |

It is certified that error appears in the above-identified patent and that said Letters Patent is hereby corrected as shown below:

On the Title Page

Item (71), Applicant:, delete "Saudi Arabia Oil Company" and insert --Saudi Arabian Oil Company-- therefor.

Item (73), Assignee:, delete "Saudi Arabia Oil Company" and insert --Saudi Arabian Oil Company-- therefor.

Signed and Sealed this
Tenth Day of October, 2023

Katherine Kelly Vidal
*Director of the United States Patent and Trademark Office*